United States Patent

Putnam, Jr.

[11] Patent Number: 5,291,774
[45] Date of Patent: Mar. 8, 1994

[54] TENNIS BALL TESTER

[76] Inventor: Charles E. Putnam, Jr., 7400 Crestway #511, San Antonio, Tex. 78239

[21] Appl. No.: 48,461

[22] Filed: Apr. 14, 1993

[51] Int. Cl.⁵ ............................................. G01N 3/48
[52] U.S. Cl. ............................................................ 73/82
[58] Field of Search ................................ 73/81, 82, 818

[56] References Cited

U.S. PATENT DOCUMENTS 4,136,554  1/1979  Larson ................................. 73/81
5,222,391  6/1993  Reenstra ............................... 73/81

Primary Examiner—Robert Raevis

[57] ABSTRACT

A means of testing used tennis balls by inserting them between a compression arm with a pressure point midway of the ball and a base with backstop which also engages the ball. The weighted compression arm is allowed to fall on the ball and a reading is obtained at the forward end of the tester to determine if the ball is playable, practicable or should be discarded.

1 Claim, 1 Drawing Sheet

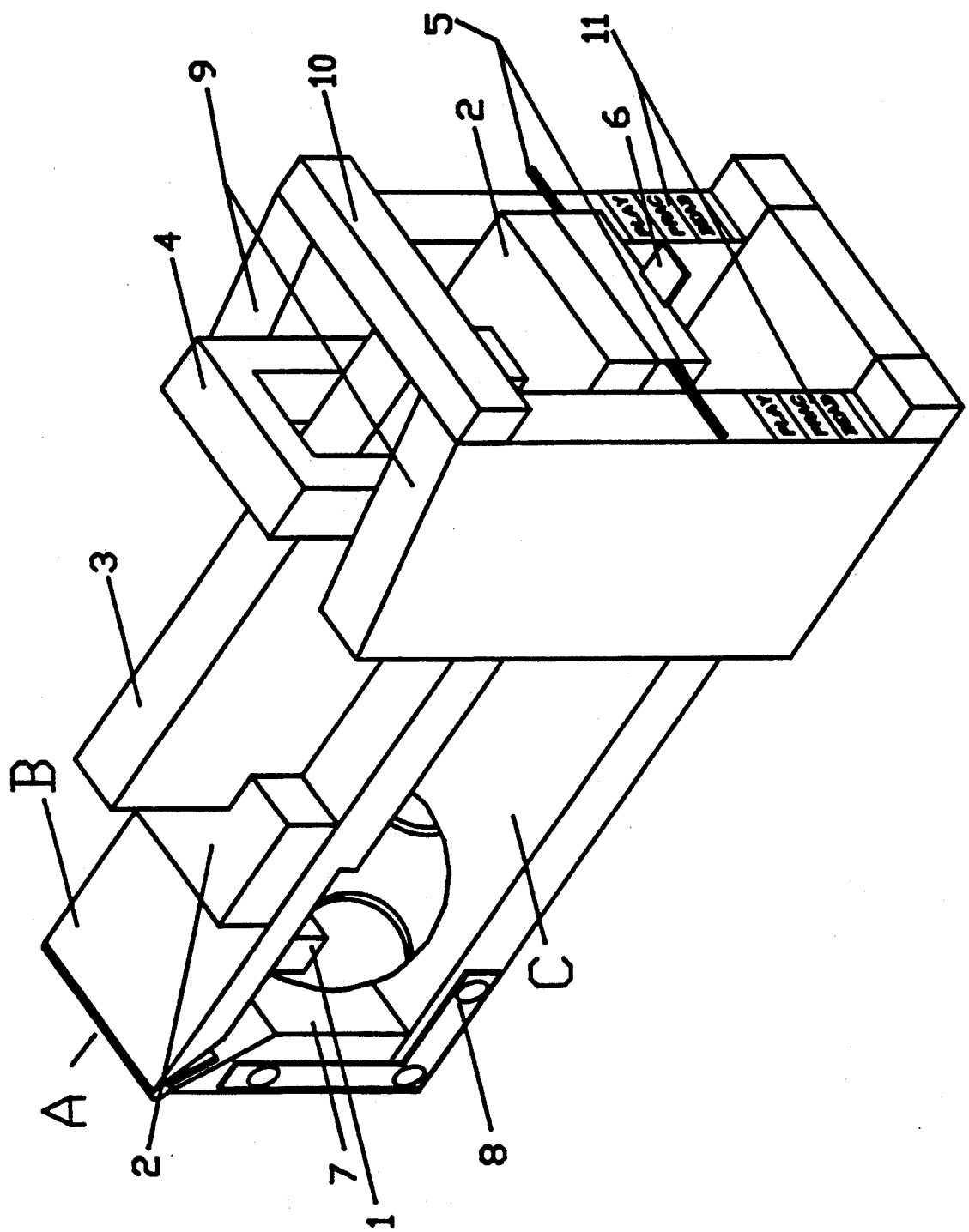

TENNIS BALL TESTER

BACKGROUND: FIELD OF INVENTION

This invention relates to tennis equipment. Specifically a device to test used tennis balls for further serviceability.

BACKGROUND: DESCRIPTION OF PRIOR ART

As newly appointed manager of a limited tennis program at the Army Residence Community at this address, I was faced with an ongoing argument as to which balls were still good enough for competitive play, which were good enough for our practice machine and which should be discarded. The two tests enployed, either squeezing the ball with the hand or dropping the ball from the level of one's nose to a hard surface and observing if it bounced waist high were imprecise at best.

The underwhelming precision of both testing measures led me to search various sporting goods outlets for some device to test used tennis balls. To the best of my knowledge none is available on the market.

I invented the Tennis Ball Tester. This quelled all argument at our facility on the subject. The Tester works convincingly and effectively.

I purchased David Pressman's book, "Patent It Yourself" as recommended by the Univ. Of Texas Patent Library. I have attempted to follow the guidelines therein as closely as possible. I did a search of the patent manuals at the library as well as one of your CASSIS system and found no conflict with my invention in either reference.

I corresponded wit the Wilson Sporting Goods Co. in River Grove Ill. and found that they use a very sophisticated instrument called a "Stevenson Deflectometer" to test their new production tennis balls. This determines whether or not the balls meet the specifications of the United States Tennis Association to qualify for use in tournaments sanctioned by that organization.

At the outset I calibrated my Tennis Ball Tester by using several new balls with the seal of approval of the UTSA by setting the top of the serviceability scale at the point where a new ball registers on the scale. So far this has proved to be consistent with five categories of new balls of different manufacturers.

OBJECTS AND ADVANTAGES

The object of the Tennis Ball Tester is to provide a reasonably precise measurement of used tennis balls for further use.

The advantage over traditional testing methods are simplicity and accuracy. The advantage over production methods is low cost.

BRIEF DESCRIPTION OF THE FIGURE AND IMPORTANT DIMENSIONS

The perspective drawing is conceptual. The legend is referred to throughout this application and is consistent. Reference letters and numerals in drawing: Letters were assigned to the three distinct elements of the inventions. Numbers were assigned to identify separate parts and functions of those-elements.
A. Hinge 2 In. wide.
B. Compression arm. 11¾ in. long.
 1. Pressure pad. ½ in. deep.
 2. weight retainer
 3. Weight. 6 lb. 7⅜ in long, 1¼ in. wide, 2¾ in deep.
 4. Weight yoke.
 5. Indicator needles. ⅜ in. from end of compression arm.
 6. Arm lifter. A ¼ in. screw eye on the prototype.
C. Base. 11½ in. long.
 7. Backstop. 3 in high.
 8. Reinforcing Brackets. 3 in.
 9. Housing. 7 in. high at front.
 10. Connecting member. ⅜ deep.
 11. Serviceability scale.
Distance between Base and bottom of pressure pad is 2½ in. when base and compression arm are horizontal.

DESCRIPTION OF STRUCTURE OF INVENTION

The Tennis Ball Tester consists of three basic parts: A hinge (A), a Compression Arm (B) and a Base (C).

The Hinge (A) simply connects the Compression Arm (B) and the Base (C).

The Compression Arm (B) which is hinged by (A) to the Backstop (7) at the rear is essentially a horizontal section which carries the Weight (3) which in turn is held in place by a Yoke (4) and front and rear retainers (2). Indicator Needles (5) protrude from the forward sides of the Compression Arm (B) which provide the reading on the Serviceability Scale (11). A Lifter (6) at the front end of the Compression Arm (b) facilities raising the Arm (B) for insertion of a ball to be tested. Toward the rear of Arm (B) is the Pressure Pad (1) which engages the tennis ball when the Arm (B) is lowered.

The Base (C) has an upright Backstop (7), a flat horizontal bottom member, a forward upright Housing (9) connected at the top front by a bracing member (10) which serves as a finger or thumb brace when raising the Compression arm.(B). The front of the Housing (9) carries a serviceability scale (11) labeled with the words PLay, Prac. (Practice) and Dead (Discard)

HOW THE INVENTION WORKS

Raising the compression arm (B) by the lifter (6) a used tennis ball is inserted at the rear of the Tester between the compression arm (B) and at the base against the backstop (7). The compression arm (B) is lowered. The pressure pad (1) on the arm engages the ball, forcing it against the backstop (7). The depression of the ball by the pressure pad (1) is multiplied approximately five times by the length of the compression arm (B). This results in placement of the indicator needles (5) over the face of the serviceability scale which indicates the condition of the ball.

It should be noted that the placement of the scale, except for the top of the "Play" zone which is that of a new ball, is arbitrary depending on the level of play at the facility where the Tester is being used.

CONCLUSION

If afforded a patent on the Tennis Ball Tester I envision this device in use at tennis clubs, institutions where costs are carefully considered such as retirement communities, schools at all levels and in municipal programs.

The response I have received at sporting goods autlets, tennis facilities and retirement communities has been encouraging. Typical tennis professional said "Hey! I can have a kid test all the balls in the machines, I wont have to squeeze them all anymore. He had eight machines.

Commercially the Tester will be made from two basic molds for hard plastic, plus the weight, hinge pin and adjustable serviceability scales. Preliminary discussion with local plastic plastic fabricators indicate no problem and reasonable cost.

One advantage that has accrued through use of the Tester besides settling local argument, I was able to prove that one brand of tennis ball, though it cost half again as much as another brand lasted more than twice as long. We switched brands.

I claim:

1. A tennis ball testing apparatus, comprising: a base (C), including an elongated horizontal bottom member, a vertically extending backstop 7 connected to a first end of the bottom member, and a pair of vertically extending housing members (9) having lower ends that are respectively connected to opposite sides of the bottom member adjacent to the second opposite end of the bottom member, each of said housing members including indicia (11) on the front of the respective housing members such that the indicia of both housing members are simultaneously viewable from a front of the apparatus, and a horizontally positioned connecting member (10) whose ends are respectively fixed to the upper ends of the housing members (9); and a compression arm assembly (B), including an elongated compression arm having a first end pivotally connected to the upper end of the backstop 7, a pair of horizontally extending indicator means (5) extending away from opposite sides of the compression arm adjacent to the second opposite end of the compression arm, said compression arm extending above the bottom member from the backstop (7) to a position passed the housing members, an arm lifter (6) coupled to the second end of the arm and projecting away from the arm towards the front of the apparatus, a weight (3) located on the upper surface of the compression arm, and a pressure member (1) attached to the lower surface of the compression arm adjacent the first end of the compression arm; whereby the backstop (7) comprises a means to permit consistent positioning of tennis balls to be tested between the pressure member (1) and upper surface of the bottom member; whereby said arm lifter (6) and said connecting member (10) together comprise a means to permit the compression arm to be raised away from the upper surface of the bottom member with a single operator hand; and whereby the indicator means and indicia of the front of the housing members together comprise a means to provide an indication of the condition of a tennis ball to be tested.

* * * * *